United States Patent [19]

Roscher et al.

[11] Patent Number: 5,475,128
[45] Date of Patent: Dec. 12, 1995

[54] PROCESS FOR PREPARING DIALKYL VINYLPHOSPHONATES

[75] Inventors: Günter Roscher, Kelkheim; Wolf-Dietmar Kaufmann, Kronberg; Bernd Laugwitz, Bad Soden, all of Germany

[73] Assignee: Hoechst Aktiengesellschaft, Frankfurt, Germany

[21] Appl. No.: 353,676

[22] Filed: Dec. 12, 1994

[30] Foreign Application Priority Data

Dec. 14, 1993 [DE] Germany ............... 43 42 570.4

[51] Int. Cl.⁶ .................... C07F 9/38; C07F 9/40
[52] U.S. Cl. ........................ 558/142; 558/217
[58] Field of Search ................................ 558/142

[56] References Cited

U.S. PATENT DOCUMENTS

| | | |
|---|---|---|
| 4,388,252 | 6/1983 | Dursch et al. . |
| 4,493,803 | 1/1985 | Kleiner et al. . |
| 4,894,470 | 1/1990 | Roscher et al. . |
| 5,132,444 | 7/1992 | Northemann et al. . |

FOREIGN PATENT DOCUMENTS

| | | |
|---|---|---|
| 0032663 | 1/1981 | European Pat. Off. . |
| 0065739 | 12/1982 | European Pat. Off. . |
| 0281122 | 9/1988 | European Pat. Off. . |
| 0456049 | 11/1991 | European Pat. Off. . |

*Primary Examiner*—Johann Richter
*Assistant Examiner*—Michael G. Ambrose
*Attorney, Agent, or Firm*—Connolly & Hutz

[57] ABSTRACT

Process for the continuous preparation of dialkyl vinylphosphonates using catalysts at temperatures of from 150° to 270° C. by dissociation of dialkyl acetoxyethanephosphonates at a pressure of from 5 to 500 mbar in contact with a liquid, catalytically active medium while drawing off the dialkyl vinylphosphonates formed and other volatile reaction products as vapors, by conveying the liquid medium in forced circulation via an evaporator while feeding in fresh dialkyl acetoxyethanephosphonate, if desired admixed with catalyst, corresponding to the distillation of dialkyl vinylphosphonates and other volatile compounds, and drawing off non-volatile material formed as byproduct from the liquid circuit to maintain constant conditions.

11 Claims, 2 Drawing Sheets

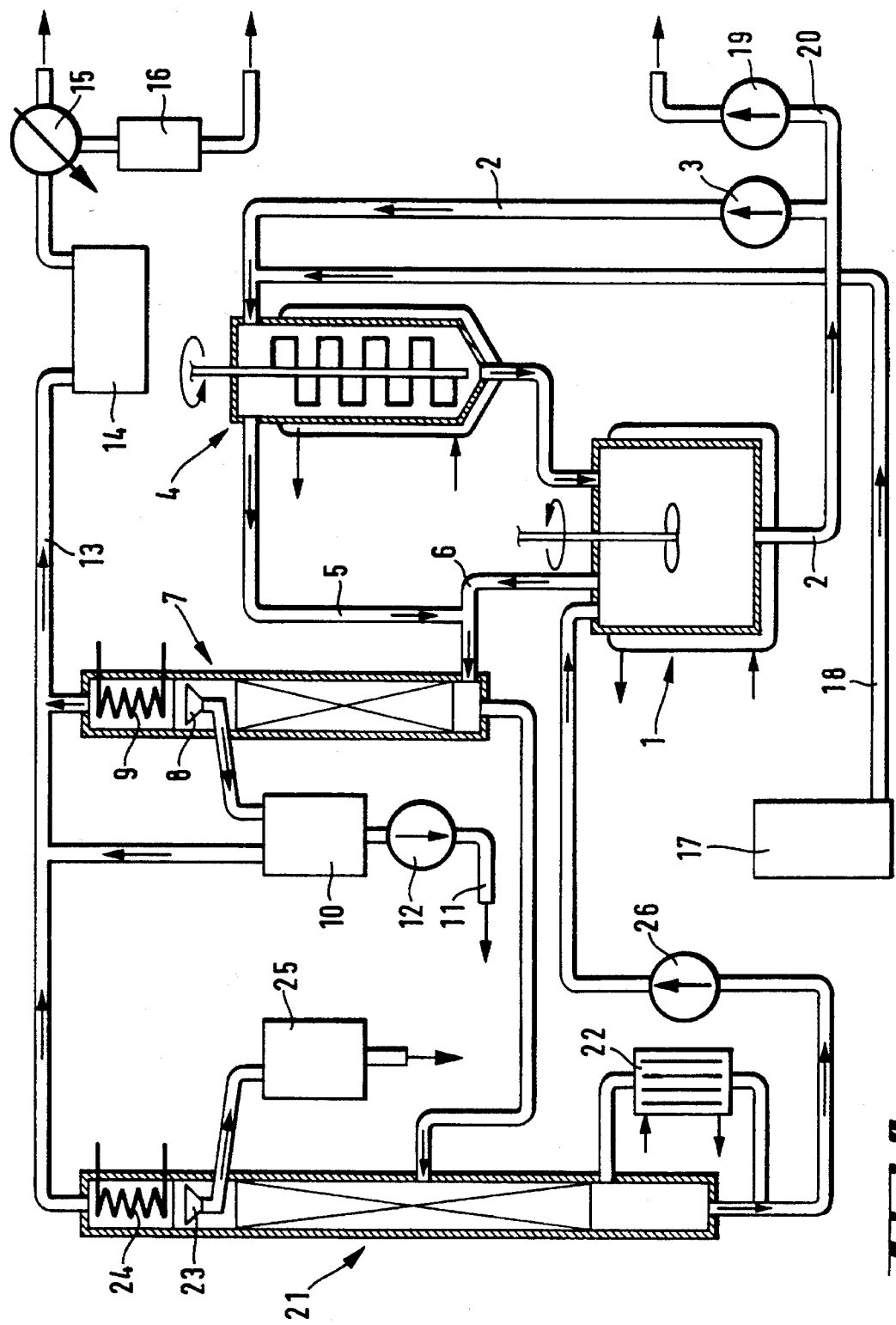

PROCESS FOR PREPARING DIALKYL VINYLPHOSPHONATES

Dialkyl vinylphosphonates are important as precursors for the preparation of pure vinylphosphonic acid and also as monomers for copolymerization for the production of adhesives or fire-resistant plastics. They can be prepared in different ways (DE-A 30 01 894, EP 281 122). According to a process described in EP 281 122, acetoxyethanephosphonic ester is thermally dissociated in the liquid phase in vacuo to give acetic acid and dialkyl vinylphosphonate, with the acetic acid and dialkyl vinyl-phosphonate distilling out of the reaction mixture. According to the procedure described, dialkyl acetoxyethanephosphonate containing, for example, vinyl-phosphonic acid (as catalyst) is introduced dropwise into a reaction flask (fitted with superposed distillation column, vacuum connection, distillate receiver, receiver for discharge of bottoms). Acetic acid and dialkyl vinylphosphonate formed are distilled off. In continuous operation, an equilibrium state is maintained by also taking off liquid-phase material according to the formation of high boilers. The yields indicated are 80% of the dialkyl acetoxyethanephosphonate reacted.

It has been found that, using the arrangement described, the yields become significantly smaller on going from the laboratory scale to an industrial scale, so that, for economic reasons owing to the yield being too small, a certain batch size cannot be exceeded using the arrangement described.

There was therefore a great need for a process in which scale-up to the industrial scale is readily possible and which makes it possible to obtain dialkyl vinylphosphonates in high yield.

This object is achieved by a process for the continuous preparation of dialkyl vinylphosphonates using catalysts at temperatures of from 150° to 270° C. by dissociation of dialkyl acetoxyethanephosphonates at a pressure of from 5 to 500 mbar in contact with a liquid, catalytically active medium while drawing off the dialkyl vinylphosphonates formed and other volatile reaction products as vapors, which comprises conveying the liquid medium in forced circulation via an evaporator while feeding in fresh dialkyl acetoxyethanephosphonate, if desired admixed with catalyst, corresponding to the distillation of dialkyl vinylphosphonates and other volatile compounds, and drawing off non-volatile material formed as byproduct from the liquid circuit to maintain constant conditions.

Various embodiments are possible for carrying out the process. Thus, for example, the circulation of the catalyst can be carried out via a normal tube exchanger having an auxiliary vessel for maintaining the level and a vapor pipe, connected to the evaporator, fitted with condenser and vacuum connection. Other experimental arrangements are also possible. Thus, it has proven useful in many cases to carry out the circulation of the catalyst via the combination of a stirred vessel with a thin-film evaporator or downdraft evaporator.

Suitable catalytically active media are the same ones as are also specified in DE-A 31 20 427 and EP 281 122, both acid and basic. Suitable acid media are, for example, sulfuric acid, phosphoric acid, halogen-containing carboxylic acids such as dichloroacetic and trichloroacetic acid and also trifluoroacetic acid, aromatic sulfonic acids such as benzenesulfonic and p-toluenesulfonic acid, vinylphosphonic acid, but in particular products which are obtained from the byproducts formed in the liquid phase in the present reaction, i.e. relatively high-boiling byproducts, by thermal treatment with water, the water treatment being able to be carried out, for example, by boiling for a period of from 5 minutes to 2 hours. Basic media which can be used are, for example, tertiary aliphatic and aromatic amines and phosphanes (in the past described as phosphines), as are likewise specified in a great number in DE-A 31 20 437.

The vapors formed as reaction product comprise dialkyl vinylphosphonate formed, acetic acid formed and also unreacted dialkyl acetoxyethanephosphonate which, in accordance with its partial pressure, also vaporizes under the reaction conditions. The vapors are advantageously introduced into a distillation column in which acetic acid and dialkyl vinylphosphonate distill via the top of the column and the liquid phase runs back into the reaction system. If the distillation column has no stripper section having additional heating, this liquid-phase runback also contains dialkyl vinylphosphonate and acetic acid in addition to unreacted dialkyl acetoxyethanephosphonate. If the downstream distillation column is provided with a stripper section having additional liquid-phase heating, the liquid phase recirculated into the reaction system can be obtained virtually free of dialkyl vinylphosphonate. The circulation of catalyst can be conducted differently. It can be conveyed from the stirred reactor via the thin-film evaporator back to the stirred reactor cocurrently with the vapors, so that the vaporized dissociation products are introduced via the gas space of the reactor into the downstream column. However, it is more favorable to draw off the vaporized dissociation products in countercurrent from the top of the thin-film evaporator and subsequently to introduce them together with the vaporized material from the stirred reactor into the downstream distillation column. It is also possible to introduce these vapor streams into two separate distillation columns. The stirred reactor alone without the circulation of catalyst via the thin-film evaporator gives, as described, only poor yields.

With circulation of catalyst via the thin-film evaporator alone without the stirred reactor, only very small throughputs are achieved.

BRIEF DESCRIPTION OF THE DRAWINGS

FIGS. 1 and 2 are diagrammatic representations of apparatuses according to the present invention.

Figure 1:
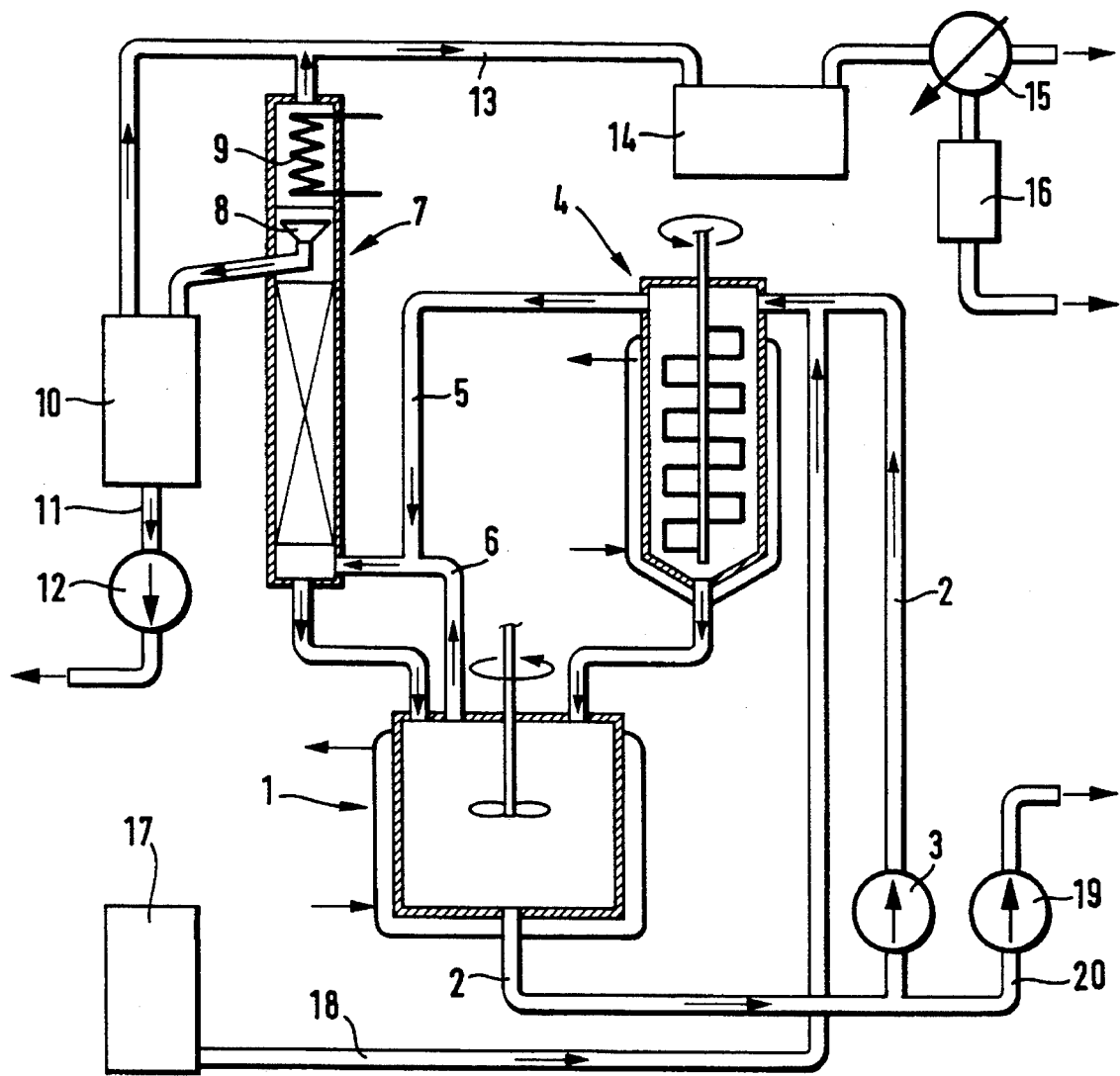

The following examples illustrate the process without restricting it to them.

COMPARATIVE EXAMPLES a) Example 1 (corresponds to Example 2 of EP 281 122)

50 g of crude vinylphosphonic acid are placed in a 1 l stirred flask fitted with a drawing-off facility for the bottoms and a distillation column (internal diameter 25 mm, length 0.7 m, packed with 6 mm Raschig rings) attached onto it and having an automatic runback divider, distillation receiver, down-stream cold trap (cooling with dry ice) and connected vacuum pump. After heating to 210° C. at a pressure of 10 mbar, a mixture of 95% by weight of dimethyl acetoxyethanephosphonate and 5% by weight of vinylphosphonic acid is metered in at a rate of about 140 g/h. After establishment of constant conditions, the level of the liquid phase in the reaction flask is kept constant by continually draining liquid-phase material into a vessel which is likewise evacuated. The reflux ratio in the column is set to 1.

Over a period of 40 hours, 5500 g are introduced. This gives 3200 g of distillate, 1020 g of product from the cold trap and 1225 g of material which is drained from the bottom.

The bottoms can, after boiling with water and distilling off the water, be again added to the starting mixture as catalyst for the dissociation. The distillate contains 89% by weight of dimethyl vinylphosphonate and 1.1% by weight of methyl acetate. The remainder is essentially acetic acid.

The product obtained in the cold trap contains 6% by weight of dimethyl vinylphosphonate, about 4% by weight of methanol and 3% by weight of acetic acid; the remainder is essentially methyl acetate. Based on dimethyl acetoxyethanephosphonate used, the yield of dimethyl vinylphosphonate is 80%.

b) Scale-up of stirred vessel

The experimental arrangement is similar to that in comparative example a). The stirred vessel comprises a 60 l stirred reactor having an outside jacket. The outside jacket is operated using heat transfer oil in forced circulation for heating the reactor.

A distillation column of glass is fitted on top of the reactor. The column is 2 m long and has an internal diameter of 225 mm. It is packed with 12 mm glass spirals. The column has an automatic runback divider and a condenser operated using refrigerated brine at −10° C., distillate receiver and vacuum connection. The vacuum equipment has, on the pressure side, a brine-operated condenser with separator. The stirred reactor is, in the bottom drainage connection, connected to a pump for pumping out bottoms.

The stirred reactor is initially charged with 10 kg of vinylphosphonic acid as catalyst for the dissociation. The entire system is evacuated, pressure 10 mbar. The stirred reactor is subsequently heated to 195° C. and 10 kg/h of dimethyl acetoxyethanephosphonate, containing 3% of vinylphosphonic acid as dissociation catalyst, are fed into the stirred vessel. After constant conditions are reached, the following conditions are set: Internal reactor temperature 195° C., pressure 10 mbar. Reflux ratio of distillation column 1.5, temperature at top 67° C.

| | |
|---|---|
| Bottoms drawn off: | 3.87 kg/h comprising a multi-component mixture containing, inter alia, phosphoric acid, polyphosphoric acids, monomethyl vinylphosphonate, phosphonic anhydrides |
| Distillate: | 3.6 kg/h |
| Dimethyl vinylphosphonate | 70% |
| Acetic acid | 27% |
| Methyl acetate | 3% |
| Condensate on pressure side of vacuum equipment | 2.43 kg/h |
| Methyl acetate | 86.5% |
| Dimethyl vinylphosphonate | 4% |
| Acetic acid | 7.4% |
| Dimethyl ether | 2% |

The yield of dimethyl vinylphosphonate, based on dimethyl acetoxyethanephosphonate used, is 40%.

$b_1$) Alteration of temperature:

At the same feed amounts, there is virtually no change in amount and composition of the individual streams up to a temperature of 210° C. in the stirred reactor. On lowering the temperature, the discharge at the bottom increases, strongly below 190° C.

$b_2$) Throughput amount:

Under the conditions described, an increase in the feed amount preferentially increases the outflow of bottoms without a significant increase in the dimethyl vinylphosphonate in the distillate.

EXAMPLE 2

The experimental arrangement is shown in FIG. 1.

Procedure: From the stirred vessel (1) placed on a balance, the bottoms containing the dissociation catalyst are pumped in a circuit via a line (2) containing a pump (3) via the thin-film evaporator (4) having an outflow for liquid phase into the stirred reactor (1). Both the vapors from the thin-film evaporator (4) via line (5), and the vapors from the stirred reactor (1) via line (6) are introduced into the column (7), automatic runback divider (8) and condenser (9) operated with refrigerated brine. The distillate from column 7 flows into the receiver (10) and is continually pumped away via line (11) by means of the pump (12). The runback from column (7) flows back into the stirred reactor (1). Condenser (9) and receiver (10) are connected via line (13) with the vacuum equipment (14). The pressure side of the vacuum equipment (14) leads to the condenser (15) operated with refrigerated brine and having a liquid separator (16). Fresh dialkyl acetoxyethanephosphonate is drawn from reservoir (17) via line (18) into the catalyst circulation line (2). From the catalyst circuit, high-boiling material formed is drawn off by means of the pump (19) via line (20) to keep the level in the stirred reactor (1) constant.

EXAMPLE 2a

The stirred reactor (1) is initially charged with 10 kg of vinylphosphonic acid. After heating to 100° C., circulation (amount 120 l/h) is started using the pump (3) and the temperature in the thin-film evaporator and stirred reactor (1) is taken up to 195° C. The pressure in the system is adjusted to 10 mbar using the vacuum equipment (14). From vessel (17), 10 kg/h of dimethyl acetoxyethanephosphonate containing 3% of vinylphosphonic acid are conveyed via line (18) into line (2) to the thin-film evaporator. The reflux ratio in column (7) is set to 2. The liquid-phase contents in the stirred reactor (1) are kept constant using the pump (19). After establishment of static conditions, the following conditions are obtained.

| | |
|---|---|
| Pressure: | from 10 to 12 mbar |
| Temperatures: | |
| Reactor (1) | 195° C. |
| Outflow from thin-film evaporator (4) | from 193 to 197° C. |
| Temperature in the heat transfer oil | 225° C. |
| Temperature at top of column (7) | from 68 to 70° C. |
| Reflux ratio of column (7) | 2 |
| Amounts: | |
| Distillate discharge via pump (12) | 7 kg/h |
| Dimethyl vinylphosphonate | 73% |
| Acetic acid | 25% |
| Methyl acetate and unknowns | remainder |
| Condensate, pressure side of vacuum equipment (14) Separator (16) | 1.1 kg/h |
| Methyl acetate | 77% |
| Acetic acid | 15% |
| Dimethyl ether | 5% |
| Dimethyl vinylphosphonate | 3% |
| Bottoms discharge pump (19) | 1.8 kg/h |
| Vinylphosphonic acid | 17% |
| Monomethyl vinylphosphonate | 30% |
| Phosphoric acid, polyphosphoric acids, phosphonic anhydrides | 53% |

The yield of dimethyl vinylphosphonate, based on dimethyl acetoxyethanephosphonate reacted, is 76%.

EXAMPLE 2b

Increase in amount: The feed amount of dimethyl acetoxyethanephosphonate can be increased with a corresponding increase in the temperature of the heat transfer oil.

At an oil temperature of 240° C., 195° C. can be maintained in the stirred reactor (1) up to a feed rate of 25 kg/h of dimethyl acetoxyethanephosphonate (3% of vinylphosphonic acid). At a reflux ratio of 1.5 in column (7), the individual streams in comparison with Example 1 increase corresponding to the increase in the feed of dimethyl acetoxyethanephosphonate. If the feed rate is further increased, constant conditions can no longer be established in the stirred reactor (1) and the thin-film evaporator (4), even by means of a further increase in the temperature of the heat transfer oil.

EXAMPLE 3

The experimental arrangement is shown in FIG. 2. The experimental arrangement is as in Example 1. However, the liquid-phase outlet of column (7) does not flow back into the stirred reactor (1), but is introduced into a second column (21). The inlet is in the middle, and the column is fitted with a circulation evaporator (22), a runback divider (23), a condenser (24), a receiver (25), and a vacuum connection to the vacuum equipment (14).

To keep the liquid level of column (21) constant, bottoms are pumped back to reactor (1) using the pump (26). This arrangement allows the throughput in comparison with Example 1a to be increased to 33 kg/h of dimethyl acetoxyethanephosphonate feed. The static conditions which are established are:

| | |
|---|---|
| Pressure | 10 mbar |
| Temperatures | |
| Reactor (1) | 195° C. |
| Outflow from thin-film evaporator (4) | from 193 to 198° C. |
| Temperature at top of column (7) | from 68 to 70° C. |
| Temperature at top of column (21) | 71° C. |
| Bottom temperature of column (21) | 140° C. |
| Feed from vessel (17) Dimethyl acetoxy-ethanephosphonate | 32 kg/h |
| Vinylphosphonic acid | 1 kg/h |
| Reflux ratio column (7) | 1.5 |
| Reflux ratio column (21) | 1 |
| Distillate from column (7), discharge pump (12) | 18.1 kg/h |
| Dimethyl vinylphosphonate | 66.2% |
| Acetic acid | 33.7% |
| Methyl acetate, others | 0.1% |
| Distillate from column (21) | 5.9 kg/h |
| Dimethyl vinylphosphonate | 85% |
| Acetic acid | 15% |
| Condensate on pressure side of vacuum equipment (14) | 3.7 kg/h |
| Methyl acetate | 82% |
| Acetic acid | 14% |
| Dimethyl vinylphosphonate | 0.3% |
| Dimethyl ether | 0.1% |
| Liquid-phase discharge from reactor (1), pump (19) | 5.2 kg/h |
| Vinylphosphonic acid | 19% |
| Monomethyl vinylphosphonate | 27% |
| Polymeric phosphonic acid and polyphosphoric acids | 54% |
| Recirculation of bottoms from column (21) to reactor (1) | 21 kg/h |
| Dimethyl acetoxyethane-phosphonate | 90% |
| Liquid phase from reactor (1) entrained as mist | 10% |

The yield of dimethyl vinylphosphonate based on dimethyl acetoxyethanephosphonate used is 77%.

We claim:

1. A process for the continuous preparation of dialkyl vinylphosphonates using catalysts at temperatures of from 150° to 270° C. by dissociation of dialkyl acetoxyethane phosphonates at a pressure of from 5 to 500 mbar in contact with a liquid, catalytically active medium while drawing off the dialkyl vinylphosphonates formed and other volatile reaction products as vapors, which comprises the steps of:

conveying the liquid medium in forced circulation through an evaporator while feeding in fresh dialkyl acetoxyethanephosphonate, and drawing off non-volatile material formed as byproduct from the liquid circuit to maintain constant conditions.

2. The process as claimed in claim 1, wherein the reaction is conducted in a combination of a stirred reactor with a thin-film evaporator or downdraft evaporator.

3. The process as claimed in claim 1, further comprising the step of:

introducing the reaction product vapors into a distillation column without additional heating, wherein the acetic acid formed and other readily volatile components are taken off at the top of said distillation column, and the major part of dialkyl acetoxyethanephosphonates also vaporized is recirculated from the bottom end of the column into the dissociation circuit.

4. The process as claimed in claim 3, wherein the distillation column contains an additional stripper section having liquid-phase heating in which continuing separation of the dialkyl vinylphosphonate formed occurs, whereby the reaction system has a return flow which contains only small remaining amounts of dialkyl vinylphosphonate.

5. The process as claimed in claim 2, wherein the vapors from the thin-film evaporator and stirred reactor are taken off in countercurrent to the circulation of catalyst at the upper end of the thin-film evaporator.

6. The process as claimed in claim 2, wherein the vapors formed are separately drawn off both from the thin-film evaporator and from the stirred reactor.

7. The process as claimed in claim 6, wherein the vapors separately drawn off are recombined before distillation.

8. The process as claimed in claim 1, wherein the catalytically active media used are acid or basic.

9. A process as claimed in claim 1, wherein the fresh dialkyl acetoxyethanephosphonate fed into the evaporator is admixed with a catalyst.

10. A process as claimed in claim 8, wherein mechanically catalytically active media used are acid.

11. A process as claimed in claim 8, wherein the catalytically active media are a product which has been formed in the reaction as a relatively high-boiling byproduct and then been treated hot with water.

* * * * *